United States Patent [19]

Supp et al.

[11] Patent Number: 5,310,506
[45] Date of Patent: May 10, 1994

[54] PROCESS OF PRODUCING A SYNTHESIS GAS FOR METHANOL SYNTHESIS

[75] Inventors: Emil Supp, Dietzenbach; Rainer Morgenroth, Friedrichsdorf, both of Fed. Rep. of Germany

[73] Assignee: Metallgesellschaft Aktiengesellschaft, Frankfurt am Main, Fed. Rep. of Germany

[21] Appl. No.: 120,140

[22] Filed: Sep. 10, 1993

Related U.S. Application Data

[63] Continuation of Ser. No. 922,304, Jul. 30, 1992, abandoned.

[30] Foreign Application Priority Data

Sep. 14, 1991 [DE] Fed. Rep. of Germany ....... 4130718

[51] Int. Cl.$^5$ ............................ C01B 3/38; C01B 3/36
[52] U.S. Cl. ...................................... 252/373; 568/697
[58] Field of Search .......................................... 252/373

[56] References Cited

U.S. PATENT DOCUMENTS

| | | | |
|---|---|---|---|
| 1,711,036 | 4/1929 | Beckley | 252/373 |
| 4,503,264 | 3/1985 | Al-Muddarris | 568/697 |
| 4,866,211 | 9/1989 | Brinkmeyer et al. | |

FOREIGN PATENT DOCUMENTS

| | | |
|---|---|---|
| 0067491 | 6/1982 | European Pat. Off. . |
| 0269297 | 6/1988 | European Pat. Off. . |
| 0376419 | 7/1990 | European Pat. Off. . |
| 1190071 | 4/1970 | United Kingdom ................ 518/704 |

OTHER PUBLICATIONS

Barbara Elvers, "Ullmann's Encyclopedia of Industrial Chemistry," (1989), pp. 173-174, 202-204, vol. A 12, Fifth, Completely Revised Edition.

*Primary Examiner*—Howard T. Mars
*Attorney, Agent, or Firm*—Sprung Horn Kramer & Woods

[57] ABSTRACT

In a reforming reactor operated with reactor outlet temperatures from 600° to 1300° C. and under a pressure from 10 to 100 bars, a methane-containing hydrocarbon gas is reacted with oxygen and water vapor. The reforming reactor is additionally fed with a high-hydrogen gas, which contains free hydrogen. The raw synthesis gas withdrawn from the reforming reactor is mainly composed of hydrogen, carbon monoxide and carbon dioxide. Without a removal of carbon dioxide from the raw synthesis gas, a synthesis gas is produced, which is suitable for the methanol synthesis and in which the concentrations of the components $H_2$, $CO$ and $CO_2$ have a molar ratio $(H_2-CO_2):(CO+CO_2)$, called the stoichiometric number, from 1.97 to 2.2. In case of need, the stoichiometry number can be adjusted by adding hydrogen to the raw synthesis gas coming from the reforming reactor.

2 Claims, 1 Drawing Sheet

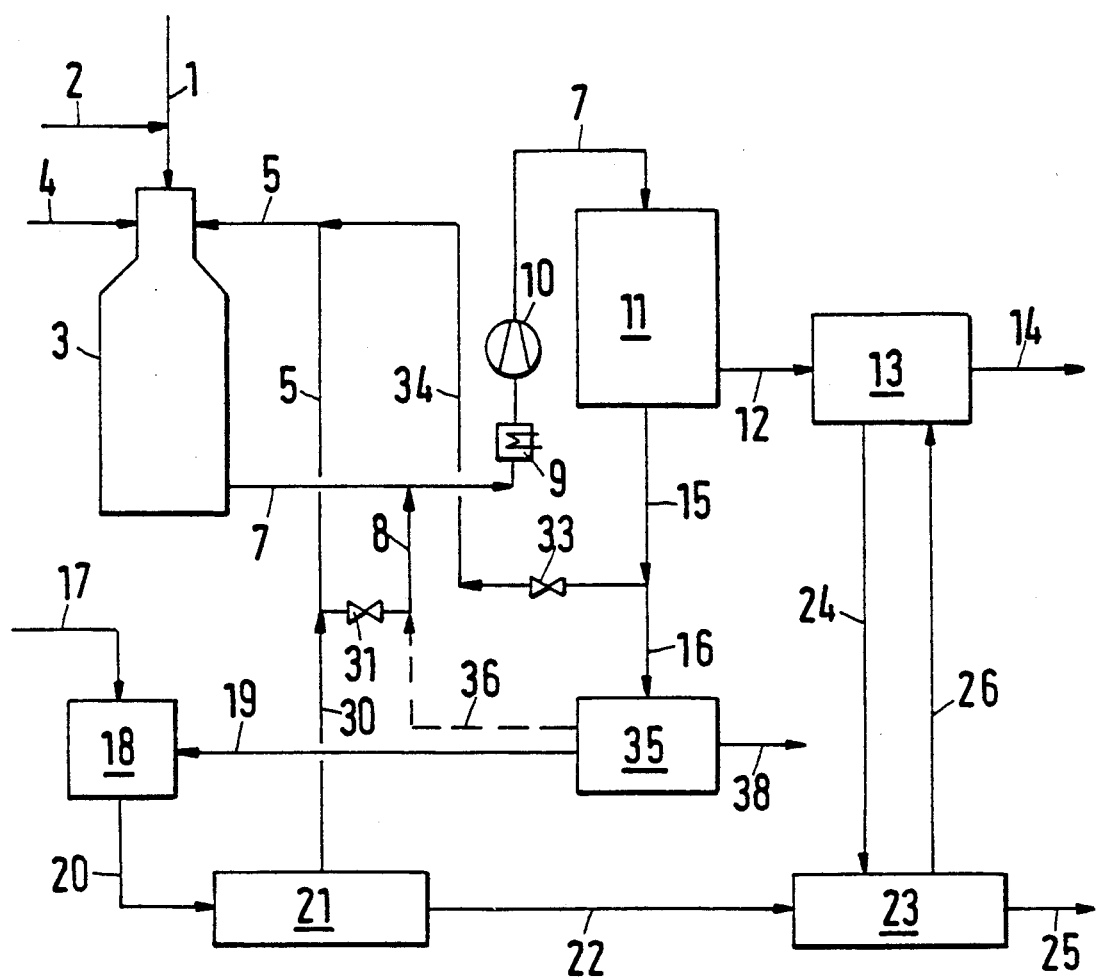

PROCESS OF PRODUCING A SYNTHESIS GAS FOR METHANOL SYNTHESIS

This application is a continuation of application Ser. No. 922,304, filed Jul. 30, 1992, now abandoned.

DESCRIPTION

This invention relates to a process of producing a synthesis gas for methanol synthesis and of reaction the synthesis gas on a catalyst to produce a high-methanol product stream, wherein a methane-containing hydrocarbon gas is subjected to an autothermic catalytic reaction with oxygen and water vapor in a reforming reactor having temperatures of 800° to 1300° C. at the reactor outlet and being under a pressure of 10 to 100 bars and a raw synthesis gas consisting mainly of hydrogen, carbon monoxide and carbon dioxide is withdrawn from the reforming reactor.

Such a process has been described in European Patent 0 067 491. Details relating to the reforming reactor for autothermic catalytic reactions are found in Ullmanns Encyclopedia of Industrial Chemistry, 5th edition, volume A12, pages 202 to 204. Information on the ideal methanol synthesis gas is furnished on pages 173 and 174 of the same volume.

It is an object of the invention to provide a most economical process of producing the synthesis gas which can be used for the methanol synthesis. In the process described hereinabove this is accomplished in accordance with the invention in that the reforming reactor for the autothermic catalytic reaction is fed with a high-hydrogen gas, which contains free hydrogen, and without removal of carbon dioxide there is produced a synthesis gas, suitable for the methanol synthesis, in which the concentrations of the components $H_2$, CO and $CO_2$ are in a molar ratio $(H_2-CO_2):(CO+CO_2)$, called the stoichiometry number of 1.97 to 2.2.

For the calculation of the stoichiometry number, the molar concentrations of hydrogen, carbon monoxide and carbon dioxide are substituted in the above equation in a manner which is known to those skilled in the art.

If high-hydrogen gas is available at a sufficiently high rate for feed to the reforming reactor, it will be possible to withdraw from the reforming reactor a raw synthesis gas which inherently has a suitable stoichiometry number so that it can be fed to the methanol synthesis reactor without further treatment. However if the gas does not yet have the desired stoichiometry number, hydrogen will be added to the raw synthesis gas at such a rate that the desired stoichiometry number is achieved.

The residual gas coming from the known methanol synthesis contains free hydrogen and oxides of carbon and must be removed from the synthesis reactor. That residual gas is desiredly fed at least in part to the reforming reactor. Alternatively the residual gas may be processed to recover at least part of the hydrogen. That hydrogen may be added to the raw synthesis gas coming from the reforming reactor in order to adjust the stoichiometry number.

According to a preferred feature of the invention, the methanol synthesis gas can be produced at particularly low cost if a high-hydrogen gas is available from another plant and can be supplied to the reforming reactor. Such high-hydrogen gases become available, e.g., in commercial dehydrogenation plants and may be used in that way.

A particularly desirable embodiment of a second process which can be combined with the process in accordance with the invention is the production of methyl-tert. butyl ether (MTBE). This is usually produced from butane, which is isomerized to form isobutane. The isobutane is dehydrogenated to form isobutylene, which is reacted with methanol to form MTBE. The high-hydrogen exhaust gas formed by the dehydrogenation is supplied at least in part to the reforming reactor. This combination of processes involves particularly low costs because the high-hydrogen exhaust gas formed by the dehydrogenation can be utilized and because methanol from the methanol synthesis is available for reacting with the isobutylene to form MTBE.

A methane-containing hydrocarbon gas, such as natural gas or oil well gas, is used in the process of the invention. In general, it is possible to use mixed gases which contain $C_1$ to $C_5$ hydrocarbons. Before the hydrocarbon gas is fed to the reforming reactor, it is desulfurized in known manner, e.g., by being passed over zinc oxide.

Oxygen is supplied to the reforming reactor at such a rate that the partial oxidation results in the desired temperature at the outlet of the reactor. Such outlet temperatures usually lie in the range from 800° to 1300° C., preferably from 850° to 1100° C. The mixed gases entering the reforming reactor are preferably at a temperature from 300° to 650° C.

In a manner known per se, steam is also supplied to the reforming reactor in order to suppress the formation of carbon black. The temperature obtained at the outlet of the reactor should desirably exceed the temperature limit for the formation of carbon black by the Boudouard reaction $(2CO \rightarrow C+CO_2)$ by more than 100° C. In the process of the invention, it is advantageous that steam is required only at a low rate. The feed mixture usually contains 1.2 to 2.0 molecules $H_2O$, 0.4 to 0.8 molecules $O_2$ and 0.2 to 0.5 molecules $H_2$ per carbon atom. The raw synthesis gas contains less than 5 mole percent and preferably less than 3 mole percent methane.

Together with the oxygen, the free hydrogen supplied to the reforming reactor accelerates the ignition in the upper portion of the reforming reactor so that the temperatures rise quickly there, as is desired, and an additional igniting catalyst or an ignition-promoting burner is not required. For this reason a catalyst-free space corresponding to 10 to 30% of the total catalyst volume may be provided in the region in which hydrogen and oxygen enter the reforming reactor.

BRIEF DESCRIPTION OF THE DRAWINGS

Further details of the invention will be explained with reference to the drawings, which is a flow sheet of the process.

A methane-containing hydrocarbon gas, such as natural gas, is supplied in line 1 and is mixed with steam from line 2, and the mixture is fed to a reforming reactor 3. The reactor 3 contains a bed of a granular nickel catalyst. Oxygen coming, e.g., from an air separation plant, not shown, is fed to the reactor 3 in line 4. A high-hydrogen gas is supplied in line 5. A pressure of 10 to 100 bars and preferably 20 to 50 bars is maintained in the reactor 3. The product of the autothermic catalytic reaction in the reforming reactor 3 is a raw synthesis gas, which is withdrawn in line 7 and has a temperature of 800° to 1300° C., preferably 850° to 1100° C., and contains methane not in excess of 3 mole percent. The concentrations of the main components hydrogen, carbon monoxide and carbon dioxide corresponds to a stoichiometry number not in excess of 2.2.

If the stoichiometry number of the synthesis gas in line 7 is not in the desired range from 1.97 to 2.2 and must be raised, this will be effected by admixing of a high-hydrogen gas coming from line 8. Without a need for a treatment for removing $CO_2$, the appropriate synthesis gas is cooled in a cooler 9 approximately to ambient temperature and is fed by a compressor 10 to the methanol synthesizer 11, which is designed in a manner known per se. A high-methanol product stream is withdrawn in line 12 and is purified in a distillation plant 13, from which the methanol product is withdrawn in line 14.

The high-hydrogen gas which is supplied in lines 5 and 8 may be produced in various ways, only some of which will be explained here. Butane from line 17 is reacted in an isomerizing plant 18 with hydrogen from line 19 too form isobutane, which is fed in line 20 to a dehydrogenation process 21. Isobutylene produced in the dehydrogenation apparatus 21 is fed by line 22 to a reactor 23 and is reacted therein with methanol from line 24. The MTBE thus produced is withdrawn in line 25. High-water methanol produced in the reactor 23 is fed by line 26 to the distillation plant 13.

A high-hydrogen exhaust gas is produced in the dehydrogenation apparatus 21 and is withdrawn in line 30 and entirely or in part is fed through line 5 to the reforming reactor 3. Part of that exhaust gas may be conducted through the valve 31 and the line 8 and added to the raw synthesis gas in line 7.

A residual gas must be removed from the methanol synthesizer 11 through 15 and may be used in various ways. In one way that exhaust gas is passed through the valve 33 and the line 34 and added to the gas in the line 5 and is thus fed to the reforming reactor 3. Alternatively, all or part of the exhaust gas may be fed in line 16 to a separation plant 35, in which a high-hydrogen gas is recovered. The separation plant 35 may be operated, e.g., to effect a pressure swing adsorption. The high-$H_2$ gas thus produced may be withdrawn in line 19 or may be conducted entirely or in part through the line 36 indicated by a dotted line and added to the gas in line 8. A methane-containing gas is withdrawn in line 38.

The conversion of butane to MTBE is known per se. Details are described in German Patent 753,753 and in Ullmanns Encyclopädie der technischen Chemie, 3rd edition, volume 10, on pages 114 to 120.

The following examples, which have been calculated in part, relate to 1 mole of $CH_4$ as a hydrocarbon gas.

EXAMPLE 1

0.28 mole $H_2$, 1.6 moles $H_2O$ 0.556 mole $O_2$ and 0.0028 mole $N_2$ are fed to the reforming reactor 3 per mole of $CH_4$. The reforming reactor 3 contains a nickel-containing catalyst. The autothermic reaction under a pressure of 65 bar and at an exit temperature of 995° C. produces a raw synthesis gas composed of

| | |
|---|---|
| $CO_2$ | 8.86 mole % |
| CO | 20.27 mole % |
| $H_2$ | 67.81 mole % |
| $CH_4$ | 2.97 mole % |
| $N_2$ | 0.09 mole % |

The stoichiometry number of that synthesis is 2.024, which means that the synthesis gas is optimally suitable for methanol synthesis.

EXAMPLE 2

1.65 moles $H_2O$, 0.686 mole $O_2$ and 0.0034 mole $N_2$ as well as 0.75 mole of an exhaust gas from a dehydrogenation per mole of $CH_4$ are subjected to the autothermic catalytic reaction described in Example 1. That exhaust gas is composed of

| | |
|---|---|
| $CO_2$ | 2.15 mole % |
| CO | 0.95 mole % |
| $H_2$ | 67.90 mole % |
| $CH_4$ | 7.15 mole % |
| $C_{2+}$ | 9.05 mole % |
| $N_2$ | 12.80 mole % |

The reactor 3 is operated under a pressure of 65 bars and at an outlet temperature of 985° C. The raw synthesis gas leaving the reforming reactor 3 is composed of

| | |
|---|---|
| $CO_2$ | 7.68 mole % |
| CO | 20.68 mole % |
| $H_2$ | 65.80 mole % |
| $CH_4$ | 3.36 mole % |
| $N_2$ | 2.48 mole % |

The stoichiometry number is 2.049 so that the synthesis gas can be used for the methanol synthesis as such, without a further treatment.

If the exhaust gas from the dehydrogenation is not used, the addition of $H_2O$ would have to be increased to 2.5 moles to prevent formation of carbon black in the reforming reactor. In that case the raw synthesis gas would have a stoichiometry number of only 1.775, which is too low.

It will be appreciated that the instant specification and claims as set forth by way of illustration and not limitation, and that various modifications and changes may be made without departing from the spirit and scope of the present invention.

What is claimed is:

1. In the production of synthesis gas for methanol synthesis and reacting the synthesis gas in the presence of a catalyst to produce a high-methanol product stream, the improvement which comprises feeding into an autothermic reforming reactor (a) a feed gas containing methane, (b) water, (c) oxygen and (d) a high-hydrogen gas which contains free hydrogen, per carbon atom in the feed gas there being supplied 1.2 to 2.0 molecules $H_2O$, 0.4 to 0.8 molecules $O_2$ and 0.2 to 0.5 molecules $H_2$, the hydrogen in said high-hydrogen gas coming at least in part from a plant other than from the instant methanol process, said reactor containing a bed of a granular nickel catalyst and a catalyst-free space above said bed, the volume of said catalyst-free space being 10–30% of the total volume of said catalyst bed, said feed gas (a), said oxygen (c) and said high-hydrogen gas (d) being fed into said catalyst-free space, autothermically reacting said feed gas in said reactor at a pressure of 10 to 100 bars, and withdrawing from said reactor a raw synthesis gas having a temperature in the range of 850° to 1100° C., said raw synthesis gas containing methane not in excess of 3 mole percent, without removal of carbon dioxide producing a synthesis gas which is suitable for the methanol synthesis in which the values of the molar ratios of the components $H_2$, CO and $CO_2$ in the formula $(H_2-CO_2):(CO+CO_2)$ is from 1.97 to 2.2.

2. A process according to claim 1, wherein a residual gas which contains free hydrogen and oxides of carbon is withdrawn from the methanol synthesis and is fed at least in part to the reforming reactor.

* * * * *